United States Patent
Onishi

(10) Patent No.: US 6,626,880 B2
(45) Date of Patent: Sep. 30, 2003

(54) BODY FLUID ABSORBENT SANITARY ARTICLE

(75) Inventor: Kazuaki Onishi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 81 days.

(21) Appl. No.: 09/821,643

(22) Filed: Mar. 30, 2001

(65) Prior Publication Data

US 2001/0037103 A1 Nov. 1, 2001

(30) Foreign Application Priority Data

Mar. 31, 2000 (JP) ........................................ 2000-099022

(51) Int. Cl.[7] .............................................. A61F 13/15
(52) U.S. Cl. ............................... 604/385.101; 604/378; 604/383
(58) Field of Search ..................... 604/385.01, 385.101, 604/378, 383, 380, 379

(56) References Cited

U.S. PATENT DOCUMENTS

| | | | |
|---|---|---|---|
| 3,908,659 A | * | 9/1975 | Wehrmeyer et al. ........ 604/374 |
| 4,276,338 A | | 6/1981 | Ludwa et al. |
| 4,323,069 A | * | 4/1982 | Ahr et al. .................. 604/378 |
| 4,780,352 A | | 10/1988 | Palumbo |
| 5,356,403 A | * | 10/1994 | Faulks et al. ............... 604/378 |
| 5,817,394 A | | 10/1998 | Alikhan et al. |
| 5,986,167 A | | 11/1999 | Arteman et al. |
| 6,441,268 B1 | * | 8/2002 | Edwardsson ................ 604/378 |

FOREIGN PATENT DOCUMENTS

| | | | |
|---|---|---|---|
| EP | 0 291 316 | * | 11/1988 |
| EP | 0 758 543 | | 2/1997 |
| EP | 0 815 819 | | 1/1998 |
| EP | 0 953 324 | | 11/1999 |
| JP | 11-318976 | | 11/1999 |

* cited by examiner

*Primary Examiner*—Weilun Lo
*Assistant Examiner*—Jacqueline F Stephens
(74) *Attorney, Agent, or Firm*—Lowe Hauptman Gilman & Berner, LLP

(57) ABSTRACT

A sanitary article includes an absorbent structure composed of a liquid-pervious topsheet, a liquid-impervious backsheet and a liquid-absorbent core disposed therebetween, an absorbent upper panel which is formed with a fibrous web and attached to an upper surface of the topsheet. The absorbent upper panel has a plurality of openings extending through the panel in its thickness direction and spaced one from another in a direction intersecting the thickness direction and a wall defining each of the openings wherein the wall has a fiber density grade which is higher in an upper region of the wall and lower in a lower region of the wall lying adjacent the topsheet.

20 Claims, 3 Drawing Sheets

BODY FLUID ABSORBENT SANITARY ARTICLE

BACKGROUND OF THE INVENTION

This invention relates to body fluid absorbent sanitary article such as a disposable diaper, a sanitary napkin, a liquid-absorbent pad for an incontinent patient or the like.

Japanese Patent Application Publication No. 1999-318976A describes a disposable diaper comprising a liquid-pervious topsheet, a liquid-impervious backsheet and a liquid-absorbent core disposed between these two sheets, longitudinally configuring front and rear waist regions and a crotch region extending between these two waist regions, wherein the diaper is formed over its approximate rear half as viewed longitudinally thereof with a plurality of ridges made of absorbent material covered with a liquid-pervious sheet. The ridges transversely extend on the inner surface of the diaper and each pair of the adjacent ridges are longitudinally spaced apart from each other by a predetermined dimension. With such known diaper, the ridges serve as barriers to restrict or prevent excretion from flowing forwardly of the diaper and at the same time to prevent excretion from leaking rearwardly of the diaper.

The Publication describes that the preventive effect for rearward leakage of excretion can be significantly improved since the absorbent material of the ridges is able to absorb moisture contained in excretion. However, it is impossible for the absorbent material of the ridges to absorb solid substances contained in excretion of high viscosity such as loose passage or liquid feces. Consequently, such solid components may stay on the outer surface of the topsheet exposed between each pair of the adjacent ridges or on the outer surface of the liquid-pervious sheet covering the ridges and these solid components may stick to a wearer's skin.

SUMMARY OF THE INVENTION

It is an object of this invention is to provide a body fluid absorbent sanitary article adapted to minimize an anxiety that excretion of high viscosity such as loose passage, liquid feces or menstrual discharge might stick to a wearer's skin.

According to this invention, there is provided a body fluid absorbent sanitary article comprising an absorbent structure which includes an absorbent core and an absorbent upper panel which is formed with a fibrous web having a compressive recovery elasticity and attached to an upper surface of the absorbent structure, the absorbent upper panel having a plurality of openings extending through the absorbent upper panel in a thickness direction thereof and spaced one from another in a direction intersecting the thickness direction and a wall defining each of the openings wherein the wall has a fiber density grade which is higher in an upper region of the wall and lower in a lower region of the wall lying adjacent an upper surface of the absorbent structure.

The body fluid absorbent sanitary article according to this invention enables high viscosity excretion such as loose passage, liquid feces and menstrual discharge to flow into the openings of the absorbent upper panel without permeating into the high density fibrous layer of the wall. Within the openings, most of a moisture content of the high viscosity excretion permeates through the topsheet into the absorbent structure and partially permeates into the low density fibrous layer. The portion of the moisture content having permeated into the low density fibrous layer moves from the low density fibrous layer toward the upper surface of the absorbent structure and permeates through the upper surface into the absorbent structure. Within the openings, a solid content of the high viscosity excretion permeates into the low density fibrous layer. In this manner, there is no anxiety that the high viscosity excretion might stay on the top surface of the panel. In other words, the high viscosity excretion is normally spaced apart from the wearer's skin and a possibility that the high viscosity excretion may stick to the wearer's skin can be minimized. Even if the panel is collapsed under the wearer's body weight, the high viscosity excretion is prevented by the high density fibrous layer of the wall from flowing back to the top surface of the panel.

Urine is absorbed by the high density fibrous layer of the wall and gradually permeates from the high density fibrous layer into the low density fibrous layer. Then, urine flows from the low density fibrous layer toward the upper surface of the absorbent structure and permeates through the upper surface into the structure. Within the openings, most of urine permeates through the upper surface into the structure and partially permeates into the low density fibrous layer. The portion of urine having permeated into the low density fibrous layer flows from the low density fibrous layer toward the upper surface of the absorbent structure and permeates through the upper surface into the structure.

DETAILED DESCRIPTION OF THE PREFERRED EMBODIMENTS

Details of a disposable diaper as an example of a body fluid absorbent sanitary article according to this invention will be more fully understood from the description given hereunder with reference to the accompanying drawings.

Figure 1:
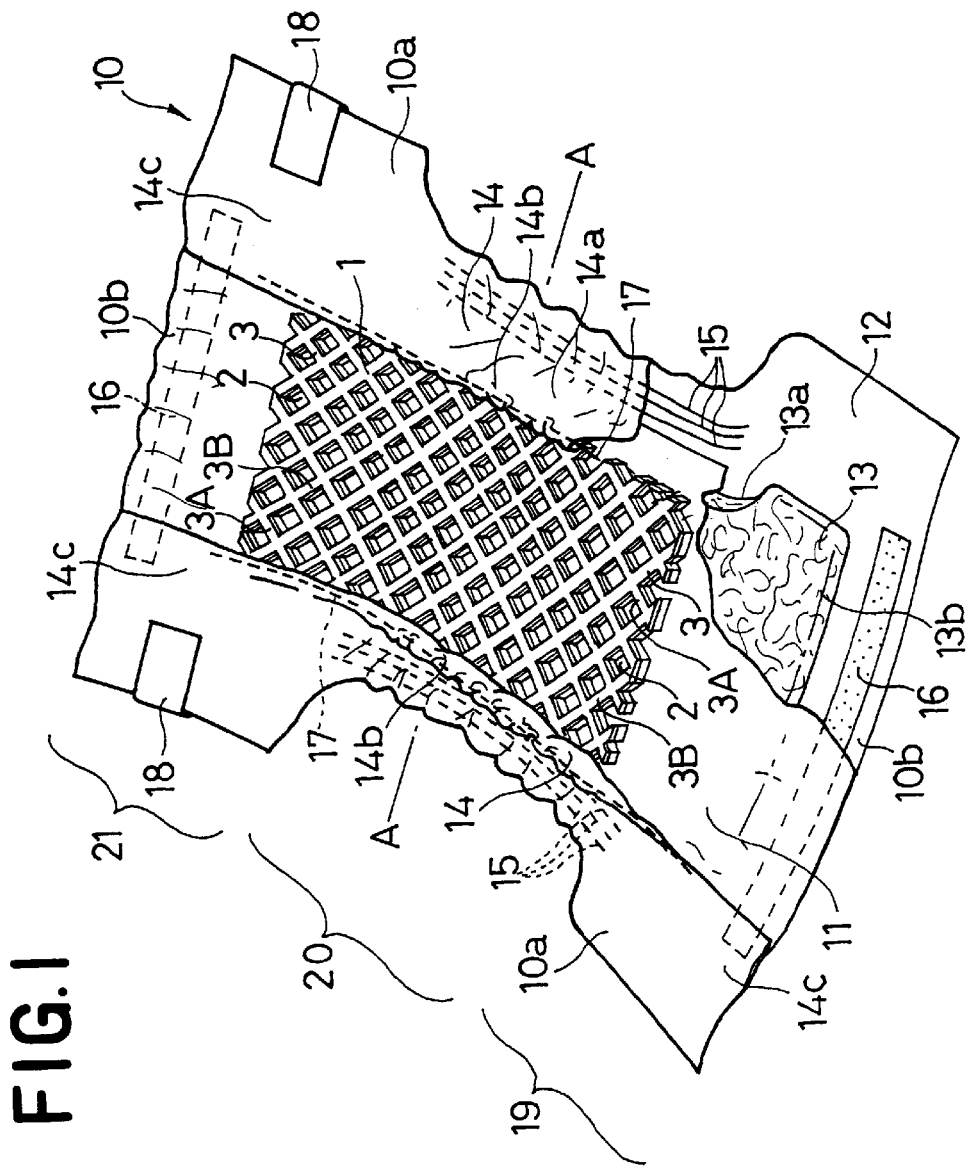
FIG. 1 is a perspective view depicting a partially cutaway diaper as one embodiment of this invention.
Figure 2:
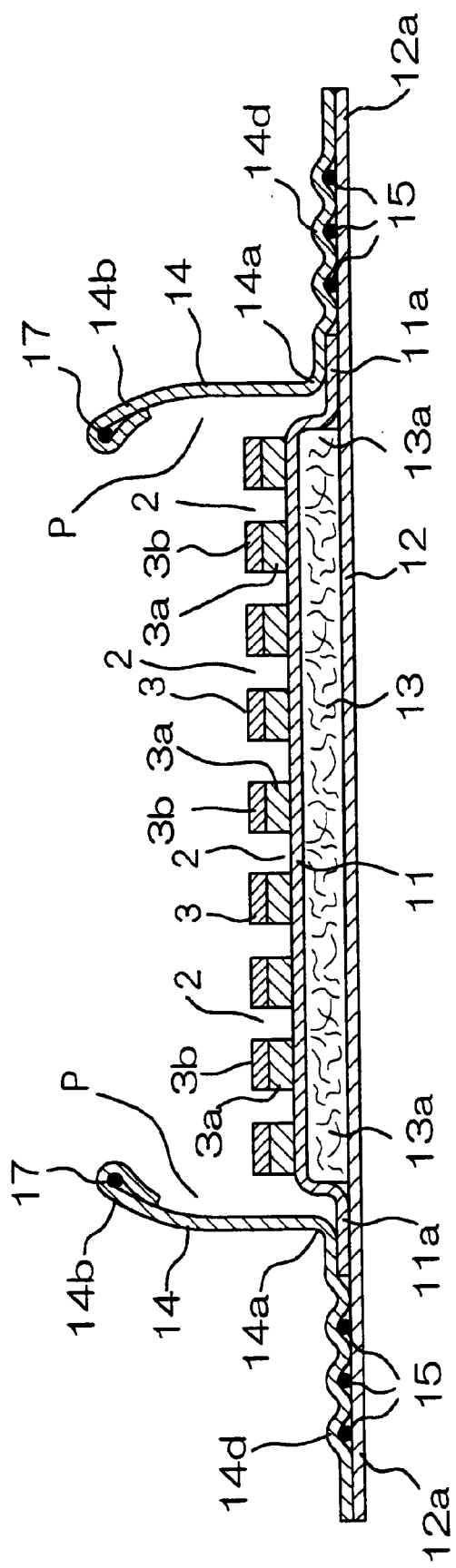
FIG. 2 is a sectional view taken along line A—A in FIG. 1.

FIG. 1 is a perspective view depicting a partially cutaway diaper 10 and FIG. 2 is a sectional view taken along line A—A in FIG. 1. The diaper 10 comprises an absorbent structure including a liquid-pervious topsheet 11 made of a hydrophilic nonwoven fabric, a liquid-impervious backsheet 12 and a liquid-absorbent core 13 disposed between these two topsheet 11 and the backsheet 12 and joined to at least one of these two sheets 11, 12. The diaper 10 configurationally comprises a front waist region 19 (first region), a rear waist region 21 (second region) and a crotch region 20 (intermediate region) extending between these front and rear waist regions 19, 21. The diaper 10 is contoured by transversely opposite side edges 10a longitudinally extending parallel to each other and curving inwardly of the diaper 10 so as to describe circular arcs in the crotch region 20 and longitudinally opposite ends 10b transversely extending parallel to each other.

The diaper 10 is provided along the transversely opposite side edges 10a with longitudinally extending thread-like elastic members 15 joined under tension thereto to be associated with leg-openings. The diaper 10 is further provided along the longitudinally opposite ends 10b with transversely extending elastic members 16 disposed between the topsheet 11 and the backsheet 12 and joined under tension to at least one of these sheets 11, 12 to be associated with a waist-opening. The diaper 10 is provided immediately outside transversely opposite side edges 13a with a pair of liquid-barrier cuffs 14 being spaced apart from each other and longitudinally extending parallel to each other.

A rectangular mat-like absorbent upper panel 1 is attached to the outer surface of the topsheet 11 so that its longer sides may be oriented longitudinally of the diaper 10. The absorbent upper panel 1 lies above a zone of the core 13 defined between the respective cuffs 14 so as to extend across the rear waist region 21 and the crotch region 20 of the diaper 10 and has its bottom surface joined to the outer surface of the topsheet 11 with an adhesive agent or heat-sealing.

The absorbent upper panel 1 is made of a fibrous web which is elastically recoverable from compressed state and has a plurality of square openings 2 extending through the absorbent upper panel in its thickness direction and a frame-like wall 3 defining the respective openings 2.

The openings 2 are spaced one from another obliquely of the transversely opposite side edges 10a as well as the longitudinally opposite ends 10b. The wall 3 comprises a plurality of first ribs 3A and a plurality of second ribs 3B. The first ribs 3A extend between each pair of the adjacent openings 2 and are spaced one from another obliquely of the transversely opposite side edges 10a as well as the longitudinally opposite ends 10b of the diaper 10. Arrangement of the second ribs 3B is similar to the arrangement of the first ribs 3A except that they are spaced one from another in the oblique direction which is orthogonal to the first ribs 3A.

Each of the openings 2 formed in the absorbent upper panel 1 is defined by a pair of the adjacent first ribs 3A and a pair of the adjacent second ribs 3B intersecting the pair of the adjacent first ribs 3A. Each of the ribs 3A, 3B has a low-density fibrous layer 3a overlying the outer surface of the topsheet 11 and a high density fibrous layer 3b overlying the low density fibrous layer 3a. The layer 3a has a fiber density lower than a fiber density of the layer 3b as well as a fiber density of the topsheet 11.

The diaper 10 is provided on the transversely opposite side edges 10a in the rear waist region 21 with respective proximal ends of tape fasteners 18 so that these tape fasteners 18 may extend transversely inward. In the front waist region 19, a rectangular target tape strip (not shown) is attached to the outer surface of the backsheet 12 so that the tape fastener 18 may be anchored on this target tape strip.

The barrier cuffs 14 lie immediately outside the transversely opposite side edges 13a of the core 13 and each of these barrier cuffs 14 has a fixed side edge portion 14a fixed to the outer surface of the topsheet 11 and extending longitudinally of the diaper 10, a free side edge portion 14b lying in the crotch region 20 and extending inward transversely of the diaper 10 under a biasing effect tending to raise the free side edge portion 14b on the diaper 10, and longitudinally opposite fixed ends 14c collapsed inward transversely of the diaper 10 and fixed, in such state, to the outer surface of the topsheet 11 in the front and rear waist regions 19, 21, respectively. A longitudinally extending elastic member 17 is joined under tension to the free side edge portion 14b of the cuff 14 so that a portion of the free side edge portion 14b may covers the elastic member 17.

Referring to FIG. 1, the diaper 10 longitudinally curves with its inner surface inside and the elastic members 15, 16, 17 relieved of tension to form gathers along the transversely opposite side edges 10a as well as the longitudinally opposite ends 10b and the respective free side edge portions 14b of the cuffs 14. In this state of the diaper 10, the topsheet 11 cooperates with the cuffs 14 to form a pair of pockets P opening inward transversely of the diaper 10.

The tape fasteners 18 have their inner surfaces coated on their free ends with a pressure-sensitive adhesive agent and may be anchored on the target tape strip with the pressure-sensitive adhesive agent to form the waist-opening and the leg-openings (not shown) of the diaper 10.

Transversely opposite side edges 11a of the topsheet 11 extend laterally outward slightly beyond the transversely opposite side edges 13a of the core 13 and the transversely opposite side edges 12a of the backsheet 12 as well as transversely outer edges of the respective cuffs 14 extend further beyond the transversely opposite side edges 11a of the topsheet 11. The transversely opposite side edges 11a of the topsheet 11 are disposed between the transversely opposite side edges 12a of the backsheet 12 and the transversely outer side edges 14d of the respective cuffs 14 and are joined to at least one the backsheet 12 and the cuffs 14. The transversely opposite side edges 12a of the backsheet 12 and the transversely outer side edges 14d of the respective cuffs 14 are placed upon and joined to each other. The elastic members 15 associated with the legs are disposed between the transversely opposite side edges 12a of the backsheet 12 and the transversely opposite side edges 14d and are attached to at least one of these side edges 12a, 14d. In the vicinity of the longitudinally opposite ends 10b of the diaper 10, respective portions of the topsheet 11, the backsheet 12 and the cuffs 14 extending longitudinally outward from longitudinally opposite ends 13b of the core 13 are placed upon and joined to one another.

Figure 3:
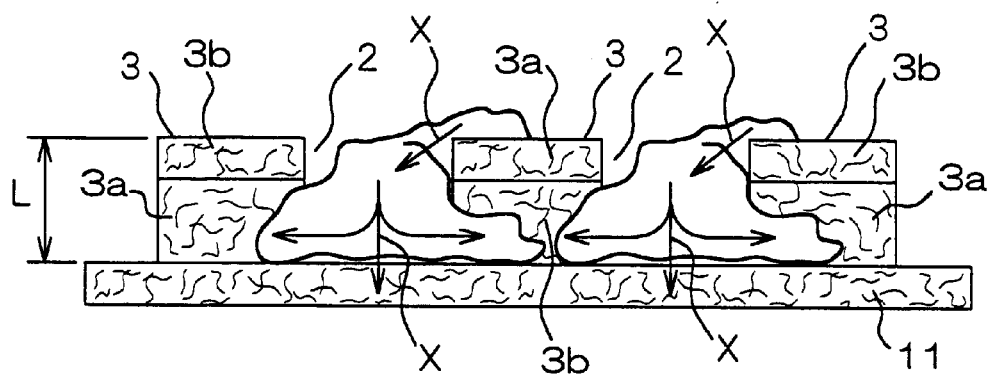
FIG. 3 is a fragmentary sectional view of an absorbent panel and a topsheet schematically illustrating a flow of loose passage.
Figure 4:
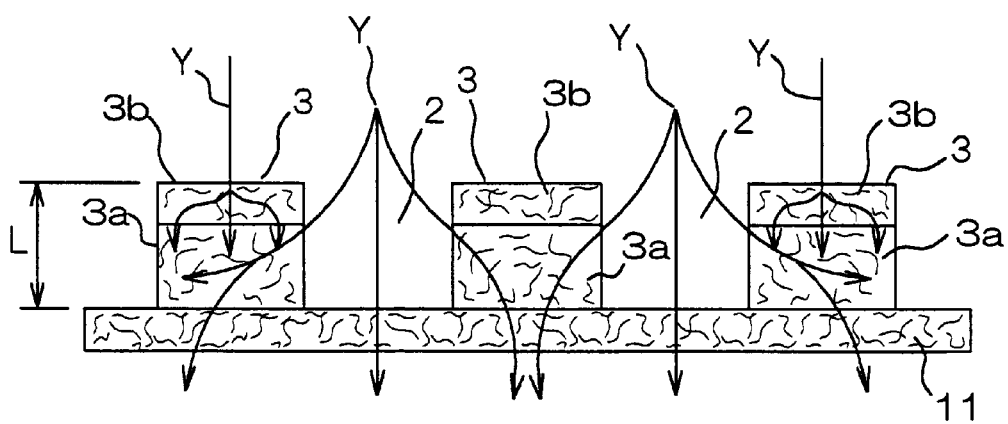
FIG. 4 is a view similar to FIG. 3 schematically illustrating a flow of urine.

FIG. 3 is a fragmentary sectional view of the panel 1 and the topsheet 11 schematically illustrating a flow of loose passage and FIG. 4 is a view similar to FIG. 3 schematically illustrating a flow of urine, in which an arrow X indicates flow of loose passage and an arrow Y indicates flow of urine. As will be apparent from FIG. 3, it is difficult for loose passage discharged onto the frame-like wall 3 to permeate into a high density fibrous layer 3b due to a relatively high viscosity and such loose passage tends to stay on a top surface of the frame-like barrier 3. However, loose passage gradually flows from the top surface into the openings 2 as the wearer's skin and the top surface of the wall 3 repeatedly rub against each other, as indicated by the arrow X. Within the openings 2, moisture content of loose passage permeates into the topsheet 11 and is absorbed by the core 13 while solid content of loose passage still staying within the openings permeates together with a portion of the moisture content into a low density fibrous layer 3a. The fibrous layer 3a has a fibrous density lower than that of the fibrous layer 3b and fibrous interstices sufficiently wider than those of the fibrous layer 3b to facilitate even the solid content of loose passage to permeate into the fibrous layer 3a. The moisture content of loose passage having permeated into the low density fibrous layer 3a then flows from this low density fibrous layer 3a toward the topsheet 11 and permeates through the topsheet 11 into the core 13. The moisture content is absorbed by the core 13 and the solid content permeates into the low density fibrous layer 3a. In this manner, loose passage is reliably spaced apart from the wearer's skin.

As illustrated in FIG. 4, urine discharged onto the panel 1, specifically onto the top surface of the wall 3 permeates into the high density fibrous layer 3b, spreads therein and then gradually permeates from the high density fibrous layer 3b into the low density fibrous layer 3a. Urine discharged into the openings 2 reaches the topsheet 11 and permeates this into the core 13. In the course of permeating through the topsheet 11, a portion of use still staying within the openings 2 permeates through the low density fibrous layer 3a of the wall 3 to the topsheet 11 and permeates through the topsheet 11 into the core 13.

A capillary effect in the topsheet 11 is higher than that in the low density fibrous layer 3a since the topsheet 11 has a fibrous density higher than that of the low density fibrous layer 3a. Such capillary effect in the topsheet 11 cooperates with an absorbency of the core 13 to guide the moisture content of loose passage and urine from the low density fibrous layer 3a toward the topsheet 11.

The barrier 3 of the absorbent upper panel 1 has a thickness L of 2~30 mm. The thickness L smaller than 2 mm would decrease a receiving capacity of the low density fibrous layer 3a of the panel 1 for loose passage so that the low density fibrous layer 3a could not receive the entire solid content of loose passage. The thickness L more than larger than 30 mm would make the wall 3 of the panel 1 bulky so that the wearer might experience a feeling of discomfort when the diaper 10 is put on the wearer's body.

Of the wall 3, the low density fibrous layer 3a has a fiber basis weight of 30~45 g/m$^2$ and a fiber density of 0.01~0.03 g/cm$^2$, and the high density fibrous layer 3b has a fiber basis weight of 45~300 g/m$^2$ and the high density fibrous layer 3b has a fiber density of 0.03~0.10 g/cm$^3$.

If the low density fibrous layer 3a has a fiber basis weight less than 30 g/m$^2$ and a fiber density less than 0.01 g/cm$^3$, a strength of the wall 3 will be decreased so that the barrier 3 may be easily collapsed under the wearer's body weight and loose passage may flow back from the low density fibrous layer 3a. If the low density fibrous layer 3a has a fiber basis weight exceeding 45 g/m$^2$ and a fiber density exceeding 0.03 g/cm$^3$, the fibrous interstices of the low density fibrous layer 3a will become dense and obstruct the solid content of loose passage from smoothly permeating into the low density fibrous layer 3a.

If the high density fibrous layer 3b has a fiber basis weight less than 45 g/m$^2$ and a fiber density of 0.03 g/cm$^3$, the fibrous interstices will become too coarse to prevent the solid content of loose passage from permeating into the high density fibrous layer 3b. With the solid content having permeated into the high density fibrous layer 3b, the solid content may turn back from the high density fibrous layer 3b to the top surface of the panel 1 as the wall 3 is compressed under the wearer's body weight. If the high density fibrous layer 3b has a fiber basis weight exceeding 300 g/m$^2$ and a fiber density exceeding 0.10 g/cm$^3$, a stiffness of the high density fibrous layer 3b will be increased and the high density fibrous layer 3b may uncomfortably stimulate the wearer's skin.

In the wall 3, the low density fibrous layer 3a has a fiber fineness of 2.2~6.5 dtex and the high density fibrous layer 3b has a fiber fineness of 0.5~2.2 dtex. The relatively high fiber fineness of the high density fibrous layer 3b enables this fibrous layer 3b to have the correspondingly dense fiber interstices.

Each of the openings 2 has an opening area of 10~1600 mm$^2$ and its occupancy ratio per unit area of the panel 1 is 20~80%. If the opening area is less than 10 mm$^2$ and the occupancy ratio is less than 20%, a receiving capacity of the openings for loose passage will be decreased and it will be impossible for the solid content of loose passage to be rapidly guided from the openings 2 into the low density fibrous layer 3a. Consequently, loose passage may stay on the top surface of the panel 1. If the opening area exceeds 1600 mm$^2$ and the occupancy ratio exceeds 80%, a strength of the barrier 3 will be decreased and the barrier 3 may be easily collapsed under the wearer's body weight.

The panel 1 has a compressive modulus represented by an equation of (a thickness under a load of 35 g/cm$^2$)÷(a thickness under a load of 2 g/cm$^2$)×100=20~80%. With the compressive modulus less than 20%, the wall 3 having been collapsed under the wearer's body weight would be unable to recover its initial state, resulting in a decreased receiving capacity of the low density fibrous layer 3a for loose passage, and it would be apprehended that loose passage might turn back from the low density fibrous layer 3a into which the loose passage has permeated. With the compressive modulus exceeding 80%, on the contrary, a stiffness of the wall 3 will increase and uncomfortably stimulate the wearer's skin.

It is possible to coat the top surface of the wall 3 with suitable water repellent. Coating with the water repellent ensures that an amount of excretion having permeated from the openings into the low density fibrous layer 3a and the high density fibrous layer 3b is reliably prevented from exuding back to the top surface of the wall 3. While the panel 1 is illustrated to extend across the rear waist region 21 and the crotch region 20, it is possible for the panel 1 to extend also into the front waist region 20.

An example of the absorbent panel 1 is made by a process comprising steps of discharging and dispersing short fibers of thermoplastic synthetic resin in air, accumulating these short fibers on a moving conveyor provided with a plurality of pins shaped in conformity of the openings so as to form a fibrous web, and subjecting the fibrous web on the moving conveyor to hot blast so that the short fibers may be fused together.

Another example of the panel 1 is made by a process comprising the steps of discharging molten thermoplastic synthetic resin from spinning nozzle, blasting air streams from gas spouts blast provided on both sides of the nozzle lip so that the molten synthetic resin may be spun by the air streams into superfine fibers, and collecting these spun fibers on a meshy moving conveyor. On the conveyor, the fibers are entangled and fused together by heat of the fibers themselves to form a fibrous web. Subsequently, the fibrous web is compressed by pressure rollers before or after cooled so that the fibrous web may be compression molded in a substantially uniform thickness.

The fiber used to form the panel 1 may be selected from a group including polyolefine-based fiber such as polypropylene or polyethylene fiber, polyester-based fiber such as polyethylene terephthalate polybutylene terephthalate, polyamide-based fiber such as nylon 66 or nylon 6, acryl-based fiber, cellulose-based fiber such as pulp, rayon or acetate, and superabsorption polymer fiber. It is also possible to disperse superabsorption polymer particles in fiber interstices of the fibrous web so that these polymer grains may be held therein. The openings 2 are not limited to the square shaped openings as illustrated but may be also provided in the other shape such as a circular, oval rectangular or triangular shape.

The structure of the panel 1 is not limited to the combination of the low density fibrous layer 3a and the high density fibrous layer 3b. It is also possible to adjust the fiber density of the wall 3 to increase continuously or discontinuously from the vicinity of the topsheet 11 toward the top surface. In the panel 1 of such alternative arrangement, the wall 3 preferably has a fiber basis weight of 30~300 g/m$^2$ and a fiber density of 0.01~0.1 g/cm$^3$. The fiber density of the barrier 3 in the vicinity of the topsheet 11 is preferably lower than that of the topsheet 11.

The backsheet 12 and the cuffs 14 may be formed with a hydrophobic nonwoven fabric, a liquid-impervious plastic film or a laminated sheet consisting of hydrophobic nonwoven fabric and a plastic film, preferably by a breathable but liquid-impervious sheet. It is also possible to use, as the stock material for the backsheet 12 and the cuffs 14, a composite nonwoven fabric (SMS nonwoven fabric) comprising a melt blown nonwoven fabric having a high water-resistance of which the opposite sheet surfaces are sandwiched between sheet surfaces of a melt blown nonwoven fabric having a high strength and a high flexibility.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric.

The component fiber of the nonwoven fabric may be selected from a group including polyolefine, polyester and polyamide fibers and conjugated fiber of polyethylene/polypropylene or polyester.

The core 13 may be formed with a mixture of fluff pulp and high absorption polymer particles compressed to a desired thickness and then entirely covered with a water-pervious sheet (not shown) such as tissue paper.

Joining of the core 13 to the sheets 11, 12, bonding of the sheets 11, 12 as well as the barrier cuffs 14 and attachment of the elastic members 15, 16, 17 may be carried out using a suitable adhesive agent such as a hot melt adhesive agent or a pressure-sensitive adhesive agent or a heat-sealing technique.

This invention is applicable not only to the disposable diaper 10 but also to a sanitary napkin or a liquid-absorbent pad for incontinent patient or the like.

What is claimed is:

1. A body fluid absorbent sanitary article, comprising:
   an absorbent structure which includes an absorbent core; and
   an upper absorbent panel which includes a fibrous web having a compressive recovery elasticity and attached to an upper surface of said absorbent structure;
   said upper absorbent panel having a plurality of openings extending through said upper absorbent panel in a thickness direction thereof and spaced one from another in a direction intersecting said thickness direction, and a wall defining said openings;
   wherein said wall has a fiber density which is higher in an upper region of said wall and lower in a lower region of said wall lying adjacent to the upper surface of said absorbent structure.

2. The sanitary article according to claim 1, wherein the upper surface of said absorbent structure has a fiber density higher than that in the lower region of said wall.

3. The sanitary article according to claim 2, wherein exposed surfaces of the upper and lower regions of said wall and exposed portions of the upper surface of said absorbent structure together define an inner face of said sanitary article which is adapted to be placed facing or adjacent to a wearer's skin in his or her crotch region, said inner face has different degrees of capillarity in a first region corresponding to the exposed surfaces of the lower region of said wall and a second region corresponding to the exposed surfaces of the upper region of said wall and the exposed portions of the upper surface of said absorbent structure.

4. The sanitary article according to claim 1, wherein said wall comprises, in the lower region, a lower density fibrous layer lying in vicinity of the upper surface of said absorbent structure, and, in the upper region, a higher density fibrous layer overlying said low density fibrous layer.

5. The sanitary article according to claim 4, wherein most fibers forming said lower density fibrous layer have a fineness of 2.2~6.5 dtex and most fibers forming said higher density fibrous layer have a fineness of 0.5~2.2 dtex.

6. The sanitary article according to claim 4, wherein the lower density fibrous layer is in contact with and sandwiched between the higher density fibrous layer and upper surface of the absorbent structure.

7. The sanitary article according to claim 6, wherein the upper surface of said absorbent structure has a fiber density higher than that in the lower region of said wall.

8. The sanitary article according to claim 1, wherein said wall has a thickness of 2~30 mm.

9. The sanitary article according to claim 1, wherein each of said openings has an opening area of 10~1600 mm$^2$ and an occupancy ratio of 20~80% per unit area of said panel.

10. The sanitary article according to claim 1, wherein said upper absorbent panel has a compressive modulus of 20~80%, said compressive modulus being determined as $$(\text{a thickness of said panel under a load of 35 g/cm2}) \div (\text{a thickness of said panel under a load of 2 g/cm2}) \times 100\%.$$

11. The sanitary article according to claim 1, wherein said absorbent structure comprises a liquid-pervious topsheet, a liquid-impervious backsheet and said liquid-absorbent core disposed therebetween to define a first region, a second region and an intermediate region extending between said first and second regions, and said upper absorbent panel being put on an upper surface of said topsheet.

12. The sanitary article according to claim 8, wherein the topsheet has a fiber density higher than that in the lower region of said wall.

13. The sanitary article according to claim 11, wherein said topsheet is made of a hydrophilic nonwoven fabric and defines the upper surface of said absorbent structure.

14. The sanitary article according to claim 1, wherein said wall extends continuously circumferentially of each of said openings to define multiple discrete said openings.

15. The sanitary article according to claim 1, wherein the lower region of said wall and the upper surface of said absorbent structure are made of different materials.

16. The sanitary article according to claim 15, wherein said wall comprises fused fibers of a thermoplastic synthetic resin, and the upper surface of said absorbent structure comprises hydrophilic nonwoven fabric.

17. The sanitary article according to claim 1, wherein the upper surface of said absorbent structure and said absorbent core are made of different materials.

18. The sanitary article according to claim 17, wherein the upper surface of said absorbent structure comprises hydrophilic nonwoven fabric, and said absorbent core comprises a mixture of fluff pulp and high absorption polymer particles.

19. The sanitary article according to claim 1, wherein said upper absorbent panel is placed on top and joined to the upper surface of said absorbent structure by adhesive or heat sealing.

20. The sanitary article according to claim 1, wherein a top, exposed surface of said wall is water repellent.

* * * * *